United States Patent
Panda et al.

(10) Patent No.: US 6,893,399 B2
(45) Date of Patent: May 17, 2005

(54) METHOD AND APPARATUS FOR B-MODE IMAGE BANDING SUPPRESSION

(75) Inventors: Satchi Panda, Fremont, CA (US); Fang F. Dong, Waukesha, WI (US); Richard Y. Chiao, Menomonee Falls, WI (US); Sastry V. S. Chilukuri, Milwauke, WI (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 0 days.

(21) Appl. No.: 10/400,879

(22) Filed: Mar. 27, 2003

(65) Prior Publication Data

US 2004/0087856 A1 May 6, 2004

Related U.S. Application Data (60) Provisional application No. 60/423,076, filed on Nov. 1, 2002.

(51) Int. Cl.[7] .............................................. A61B 8/00
(52) U.S. Cl. ..................................................... 600/443
(58) Field of Search ............................... 600/443, 437, 600/447; 73/625–626, 631, 6; 367/30, 59, 65, 98

(56) References Cited

U.S. PATENT DOCUMENTS

| | | | | |
|---|---|---|---|---|
| 4,707,813 A | * | 11/1987 | Moeller et al. ............. | 367/103 |
| 5,111,824 A | * | 5/1992 | Lazenby et al. ............. | 600/447 |
| 5,462,057 A | * | 10/1995 | Hunt et al. .................. | 600/447 |
| 5,568,813 A | * | 10/1996 | Deitrich et al. ............. | 600/447 |
| 5,579,770 A | * | 12/1996 | Finger ......................... | 600/447 |
| 5,827,189 A | * | 10/1998 | Mo et al. ..................... | 600/454 |
| 5,879,303 A | * | 3/1999 | Averkiou et al. ........... | 600/447 |
| 5,897,500 A | * | 4/1999 | Zhao ........................... | 600/443 |
| 6,056,693 A | * | 5/2000 | Haider ........................ | 600/443 |
| 6,432,056 B1 | * | 8/2002 | Cooley et al. .............. | 600/443 |
| 6,516,667 B1 | * | 2/2003 | Broad et al. ................ | 73/602 |
| 6,689,060 B2 | * | 2/2004 | Phelps et al. ............... | 600/437 |

* cited by examiner

*Primary Examiner*—Francis J. Jaworski
(74) *Attorney, Agent, or Firm*—McAndrews, Held & Malloy, Ltd.; Peter J. Vogel; Michael A. Dellapenna (57) ABSTRACT

Certain embodiments include a system and method for banding suppression in a B-mode ultrasound image. Banding occurs in a diagnostic image when two or more focal regions having different waveforms and/or frequencies, for example, are combined. The resulting difference in intensity between the focal regions produces banding in the final image. For purposes of illustration only, the method below will be described with two focal zones. Certain embodiments of the present invention reduce banding in a diagnostic image including a plurality of focal zones by processing the first focal zone, determining intensity around the border or "stitch line" between the two focal regions, and adjusting the second focal region based on the difference in intensity. Preferably, processing is done in real time as image frames are updated.

25 Claims, 5 Drawing Sheets

Apply compensation linearly from delta/2 at splicer position down to 0 at the other boundary.

METHOD AND APPARATUS FOR B-MODE IMAGE BANDING SUPPRESSION

RELATED APPLICATIONS

The present application relates to, and claims priority from, U.S. Provisional Application No. 60/423,076 filed on Nov. 1, 2002, and entitled "Method and Apparatus for B-Mode Image Banding Suppression".

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention generally relates to ultrasound imaging. In particular, the present invention relates to banding suppression in ultrasound imaging.

Ultrasound is sound having a frequency that is higher than a normal person may hear. Ultrasound imaging utilizes ultrasound waves or vibrations in the frequency spectrum above normal human hearing, such as the 2.5–MHz range. Ultrasound imaging systems transmit ultrasound into a subject, such as a patient, in short bursts. Echoes are reflected back to the system from the subject. Diagnostic images may be produced from the echoes. Ultrasound imaging techniques are similar to those used in SONAR and RADAR.

B-mode (brightness mode) imaging is a grayscale ultrasound imaging technique that constructs images based on echoes received from pulses transmitted through a cross-section of the subject scanned. In B-mode imaging, the brightness of a spot or pixel representing an echo in a grayscale image corresponds to the strength of the received echo. The voltage of an echo received at an ultrasound receiver is an indication of brightness. B-mode imaging may be used on its own or combined with Doppler imaging or another imaging technique.

Forming the best possible image at all times for different anatomies and patient types is important to diagnostic imaging systems. Poor image quality may prevent reliable analysis of the image. For example, a decrease in image contrast quality may yield an unreliable image that is not usable clinically. Additionally, the advent of real-time imaging systems has increased the importance of generating clear, high quality images. Differences between different body types may result in blurring, streaking, or introduction of ghost images or artifacts in a resulting image. Automatic optimization of diagnostic images helps to ensure consistent image quality over a wide range of patients.

Multiple focal zones are often used to improve resolution and/or penetration of an ultrasound image. A focal zone is a location within the body at which the transmitted ultrasound pulse is focused. Each focal zone has a corresponding focal region over which energy transmitted to that focal zone produces the best image. Typically, different waveforms and/or f-numbers (a ratio of lens focal length to lens aperture diameter) are used for different focal zones, and the focal region includes the focal zone. When multiple focal zones are used, an ultrasound image is formed by adjoining each focal region that corresponds to the focal zones. When two or more regions are joined together, the borders of the regions may be distinct and visible in the image. The artifactual edges are known as banding artifacts. Banding artifacts are caused by differences in speckle brightness or texture between two focal regions. Currently, transmit waveforms and depth-dependent gain curves are carefully selected to eliminate banding artifacts on the average patient. However, patient body types are diverse (particularly with pathology), and banding artifacts may occur despite the most carefully selected gain curves. Therefore, a real-time, adaptive band-suppression method is needed to reduce banding artifacts over a wide range of patient body types.

Thus, an ultrasound imaging system that automatically adjusts system parameters in real time to reduce banding on a wide range of patient body types would be highly desirable. Furthermore, a system that reduces banding in real time with faster processing than current systems would be highly desirable. A more accurate and efficient method for reducing banding would also be highly desirable. Furthermore, a method for reducing banding artifacts that is applicable to all B-mode applications would be highly desirable.

BRIEF SUMMARY OF THE INVENTION

Certain embodiments include a system and method for banding suppression in a B-mode ultrasound image. Banding occurs in a diagnostic image when two or more focal regions obtained using different waveforms and/or f-numbers, for example, are combined. The difference in image intensity between the focal regions produces banding in a composite image. For purposes of illustration only, the method below will be described with two focal zones. Certain embodiments of the present invention reduce banding in a diagnostic image including a plurality of focal zones by processing a first focal region corresponding to a first focal zone, determining intensity around a border or "stitch line" between the two focal regions, and adjusting a second focal region based on the difference in intensity. Processing is done in real time as image frames are updated.

Certain embodiments of the system include a transducer for transmitting ultrasound energy to a subject and receiving echoes from the subject, a front-end for producing data from the received echoes, and a processor for processing the data to produce an image, the processor combining data from at least a first focal zone and a second focal zone, wherein the processor determines a difference in intensity between data in first and second focal regions, the processor applying the difference to at least one of the first focal region and the second focal region.

The processor may include a B-mode processor, a control processor, and/or a display processor. The processor may accommodate a plurality of imaging and diagnostic modes. The front-end may include a receiver, a transmitter, and a beamformer. The system may also include a display for formatting and displaying the image data.

Certain embodiments of the method include examining a border between a first focal zone and a second focal zone in a combined ultrasound image, selecting a first subset of data adjacent to the border in the first focal zone and a second subset of data adjacent to the border in the second focal zone, determining a first intensity level for the first subset of data and a second intensity level for the second subset of data, determining a difference between the first intensity level and the second intensity level, and applying the difference to at least one of the first focal zone and the second focal zone.

The first and second intensity levels may be means or median intensity values for the first and second focal zones.

The difference may be split equally and applied to the first and second focal zones. In an embodiment, the difference may not be applied if a certain threshold, such as a dark pixel threshold, a minimum intensity difference threshold, or a maximum intensity difference threshold, is exceeded. The method may also include applying a filter to the combined ultrasound image. The method may further include displaying the combing ultrasound image.

Certain embodiments of the present invention include a method for banding suppression in a B-mode ultrasound system. The method includes processing a first focal region to determine intensity of first focal region image data, determining a difference in intensity between first focal region image data and second focal region image data surrounding a border between the first focal region and a second focal region, and adjusting intensity of image data in the second focal region based on the difference in intensity. The method may include determining a difference in median or mean intensity between first focal region image data and second focal region image data surrounding a border between the first focal region and a second focal region. The method may also include splitting the difference equally and applying the split different to the first and second focal regions. The image data intensity may not be adjusted if at least one of a dark pixel threshold is exceeded, the difference is less than a minimum threshold, and the difference is greater than a maximum threshold. The method may further include applying a filter to the combined ultrasound image.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Figure 1:
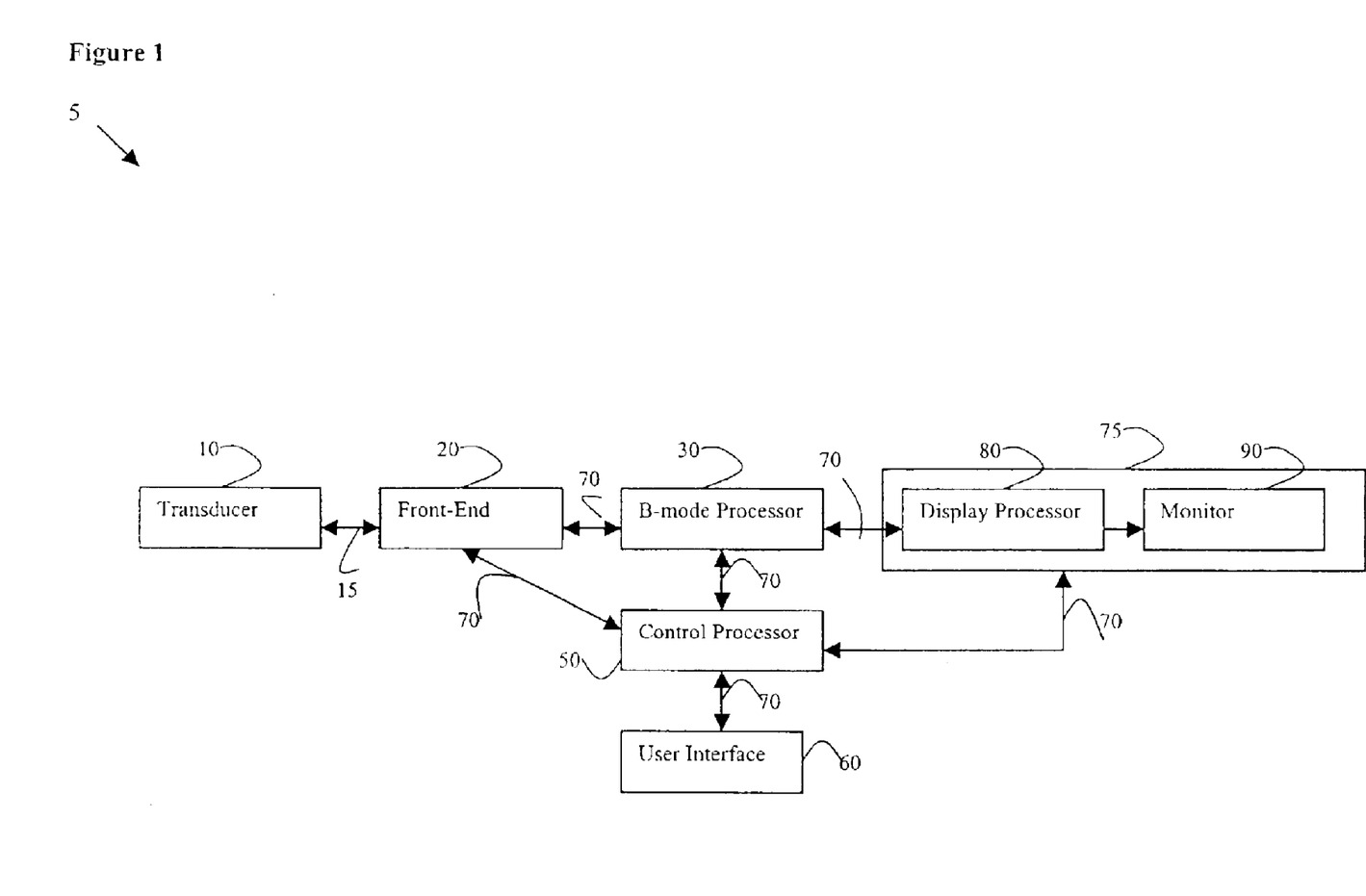
FIG. 1 illustrates a block diagram of an ultrasound imaging system that is used in accordance with an embodiment of the present invention.

FIG. 1 illustrates a block diagram of an ultrasound imaging system 5 used in accordance with an embodiment of the present invention. A transducer 10 is used to transmit ultrasound waves into a subject by converting electrical analog signals to ultrasonic energy. The transducer 10 also is used to receive ultrasound waves that are backscattered from the subject by converting ultrasonic energy to analog electrical signals. A front-end 20 including a receiver, a transmitter, and a beamformer, is used to create transmitted waveforms, beam patterns, receiver filtering techniques, and demodulation schemes that are used for various imaging modes. The front-end 20 converts digital data to analog data and vice versa. The front-end 20 interfaces with the transducer 10 via an analog interface 15. The front-end 20 interfaces with a B-mode processor 30 and a control processor 50 via a digital bus 70. The digital bus 70 may include several digital sub-buses. The digital sub-bases may have separate configurations and provide digital data interfaces to various parts of the ultrasound imaging system 5.

The B-mode processor 30 provides amplitude detection and data compression for B-mode imaging. In a certain embodiment, the B-mode processor 30 may also be used for other imaging modes, such as M-mode (motion mode), B+M-mode (both motion and brightness), harmonic imaging, and/or Doppler imaging. The B-mode processor 30 receives digital signal data from the front-end 20. The B-mode processor 30 processes the received digital signal data to produce estimated parameter values. The estimated parameter values may be produced using the received digital signal data. The digital signal data may be analyzed in frequency bands centered at the fundamental, harmonics, or sub-harmonics of the transmitted signals to produce the estimated parameter values. The B-mode processor 30 passes the estimated parameter values to a control processor 50 over the digital bus 70. The B-mode processor 30 may also pass the estimated parameter values to a display 75 via the digital bus 70.

The display 75 includes a display processor 80 and a monitor 90. The display processor 80 accepts digital parameter values from the B-mode processor 30 and the control processor 50. The display processor 80 may perform scan-conversion functions, color mapping functions, and tissue/flow arbitration functions, for example. The display processor 80 processes, maps, and formats the digital data for display, converts the digital display data to analog display signals, and passes the analog display signals to the monitor 90. The monitor 90 accepts the analog display signals from the display processor 80 and displays the resultant image. An operator may view the image on the monitor 90.

A user interface 60 allows user commands to be input by the operator to the ultrasound imaging system 5 through the control processor 50. The user interface 60 may include a keyboard, mouse, switches, knobs, buttons, track ball, and/or on screen menus, for example (not shown).

The control processor 50 is the central processor of the ultrasound imaging system 5. The control processor 50 interfaces to other components of the ultrasound imaging system 5 using the digital bus 70. The control processor 50 executes various data algorithms and functions for various imaging and diagnostic modes. Digital data and commands may be transmitted and received between the control processor 50 and other components of the ultrasound imaging system 5. In an alternative embodiment, functions performed by the control processor 50 may be performed by multiple processors and/or may be integrated into the B-mode processor 30 and/or the display processor 80. In another embodiment, the functions of the processors 30, 50, and 80 may be integrated into a single personal computer (PC) backend.

Figure 2:
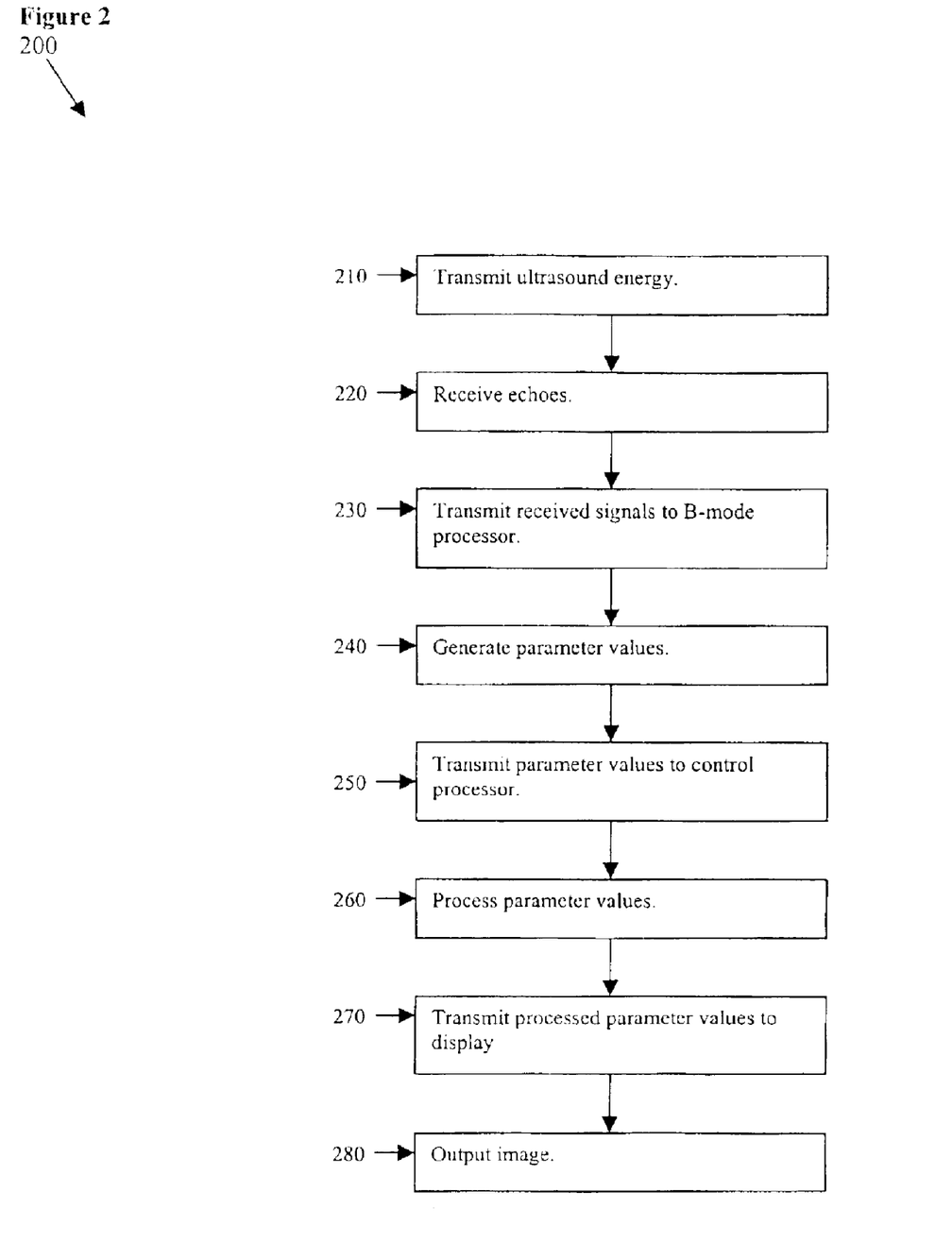
FIG. 2 illustrates a method for ultrasound imaging in accordance with an embodiment of the present invention.

FIG. 2 illustrates a method 200 for ultrasound imaging in accordance with an embodiment of the present invention. First, at step 210, the transducer 10 transmits ultrasound energy into a subject, such as a patient. Then, at step 220, ultrasound energy or echoes backscattered from the subject are received at the transducer 10. Signals are received at the front-end 20 in response to ultrasound waves backscattered from the subject.

Next, at step 230, the received signals are transmitted from the front-end 20 to the B-mode processor 30 using the digital bus 70. At step 240, the B-mode processor 30 generates parameter values based on the received signals. Then, at step 250, the parameter values are sent to the control processor 50.

At step 260, the control processor 50 processes the parameter values for use in display, storage, and diagnostics at the display 75. The control processor 50 may combine a plurality of parameter value sets from a plurality of focal zones into a single image for display. The control processor 50 processes the image data parameter values to reduce banding artifacts in the resulting combined diagnostic image. Banding reduction will be described in further detail below.

Next, at step 270, processed parameter values are transmitted to the display 75. The display processor 80 may also process parameter values from a plurality of focal zone images to produce a combined image in conjunction with and/or in addition to the control processor 50. Data processing to reduce banding resulting from differences between the focal regions will be discussed further below.

Finally, at step 280, a diagnostic image is produced and output at the monitor 90. The image may be stored, displayed, printed, and/or further transmitted, for example. The display processor 80 may produce the diagnostic image using the processed parameter values from the digital signal data.

Banding occurs in a diagnostic image when two or more focal regions having different waveforms and/or f-numbers, for example, are combined. The resulting difference in intensity between the focal regions produces banding in the final image. For purposes of illustration only, the method below will be described with two focal zones. Certain embodiments of the present invention reduce banding in a diagnostic image including a plurality of focal zones by processing the first focal zone, determining intensity around the border or "stitch line" between the two focal zones, and adjusting the second focal region based on the difference in intensity. Preferably, processing is done in real time as image frames are updated.

Figure 3:
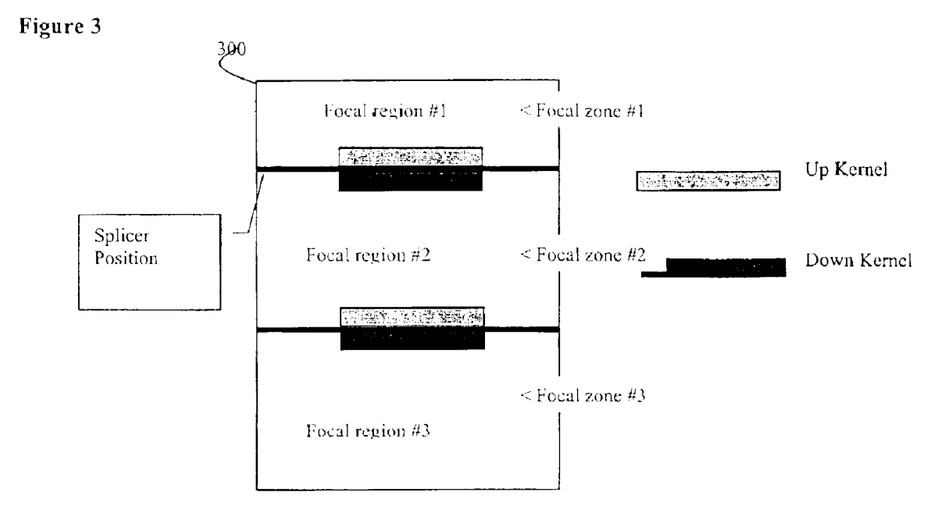
FIG. 3 shows an image with multiple focal zones and corresponding focal regions in accordance with an embodiment of the present invention.

FIG. 3 illustrates an image 300 with multiple focal zones and corresponding focal regions in accordance with au embodiment of the present invention. As indicated in FIG. 3, a splicer position is a position where a transition between the adjacent focal zones occurs. In a B-mode image, to avoid visible discontinuity at a transition region between adjacent focal zones, fading may also be applied to reduce image mismatch between adjacent zones.

Figure 4:
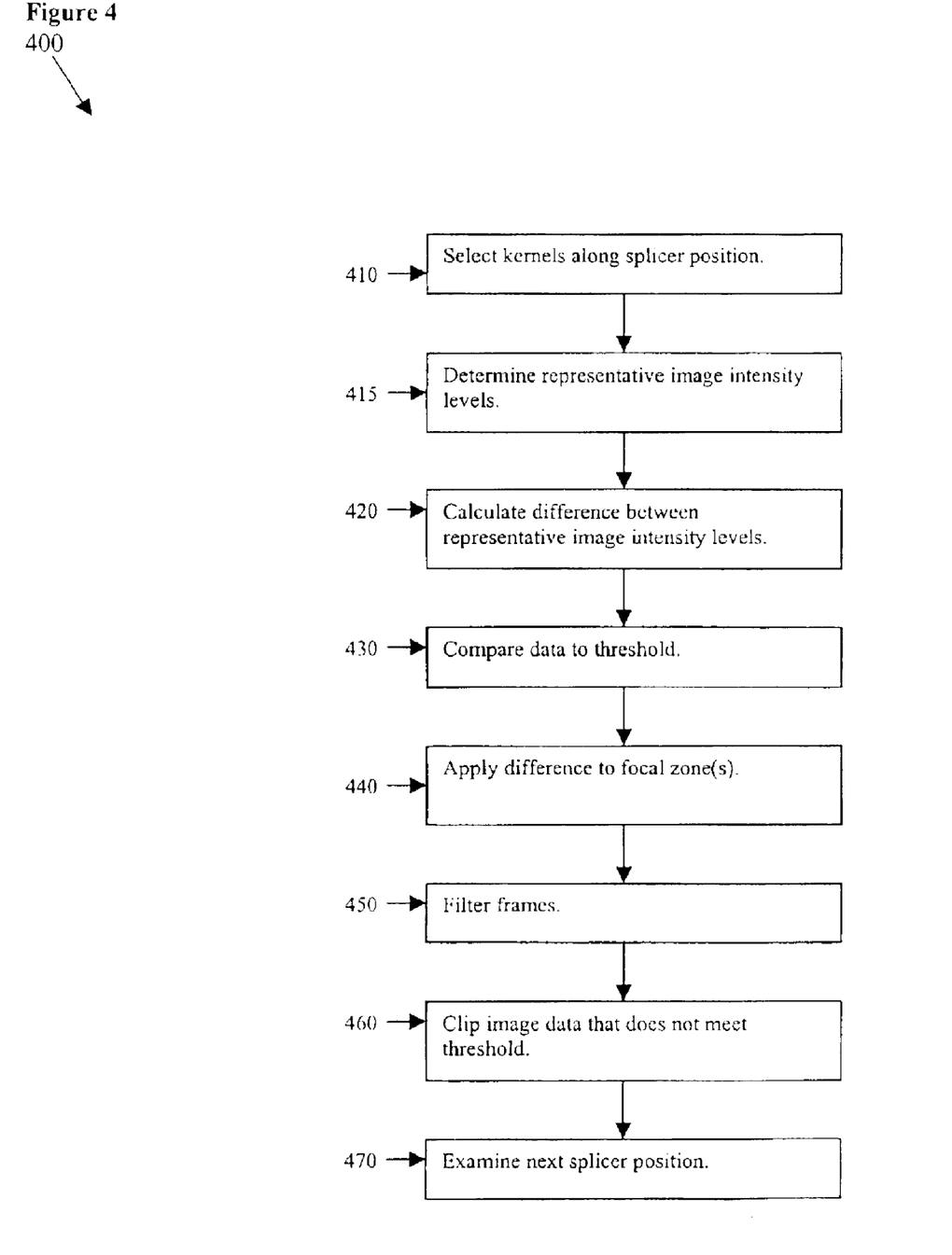
FIG. 4 illustrates a method for banding suppression in accordance with an embodiment of the present invention.

FIG. 4 illustrates a method 400 for banding suppression in accordance with an embodiment of the present invention. First, at step 410, two kernels are selected along a splicer position between two focal zones in a middle portion of an image (a combined ultrasound image, for example). The two kernels are called "Up" and "Down" kernels. In an embodiment, the vertical width of a kernel is preferably approximately 3–5 pixels wide, and the lateral width is preferably approximately 80% of the entire image width, for example. However, the exact size of a kernel does not impact the operation of the method 400. The splicer position may be included in either the "Down" or "Up" kernel, depending on configuration of the imaging scanner.

Then, at step 415, representative image intensity levels are computed for both Up and Down kernels. A median or a mean value, for example, may be used as a representative image intensity level. Since the number of bits of incoming data may be limited (for example to 8bits), an efficient median-searching method may be used.

In certain embodiments, two thresholds may be applied to determine whether a data point may be used in calculating the median of the kernel. In certain embodiments, a bright vessel boundary, a dark cystic structure, and/or blood flow may be present inside a kernel, which may bias an estimation of a median or mean value. For example, for 8 bit data (256 intensity levels), a lower intensity threshold of 10 and an upper intensity threshold of 200 may be used to exclude extreme data points. In an embodiment, the entire image may be processed to determine thresholds before applying band suppression. Methods such as histogram analysis, for example may be used to find optimal thresholds.

Then, at step 420, after representative image intensity values for both Up and Down kernels are found, a difference (or delta) between the representative image intensity value of the Up kernel and the representative image intensity value of the Down kernel is calculated.

Next, at step 430, a number of dark pixels in a kernel and/or the difference between representative image intensities may be compared to certain threshold(s) to determine if compensation may be applied to the focal zone(s). For example, in an embodiment, if the Up kernel contains a bright vessel boundary and the Down kernel contains low-scattering blood flow (or vice versa), and neither dark nor bright intensity data has been excluded by lower or upper thresholds, the difference between the representative image intensity levels may exceed a threshold, such as 30 or 50, for example. In this case, the band suppression method may be turned off to avoid creating extra banding by biased values.

In another embodiment, a threshold may be used when a kernel contains a large number of dark pixels, such as when a splicer position is partially within or aligned with a blood vessel edge, for example. If a ratio between a number of dark pixels in a kernel to a number of total pixels in a kernel (referred to as a black ratio, for example) exceeds a black ratio limit (usually set to 1), banding compensation may be ignored for the splicer position. For example, a kernel with a black ratio above the defined threshold may contain noise, blood, or fluid.

In another embodiment, if the difference between representative intensity values from Up and Down kernels is less than a difference limit, compensation may not be performed in order to save computation time. For example, a gray level difference between two zones may be less than 50 but greater than an intensity difference corresponding to 4 dB. To avoid over-compensation, a 2 dB difference may be applied to each zone, so total banding compensation will not exceed 4 dB.

At step 440, the difference in representative image intensity level may be applied to either focal zone. Preferably, the difference or compensation amount is split equally into two halves. That is, the entire compensation amount may not be applied to one focal zone. Half of the difference may be applied to each side or focal zone (one is positively compensated, and the other zone is negatively compensated, for example).

Figure 5:
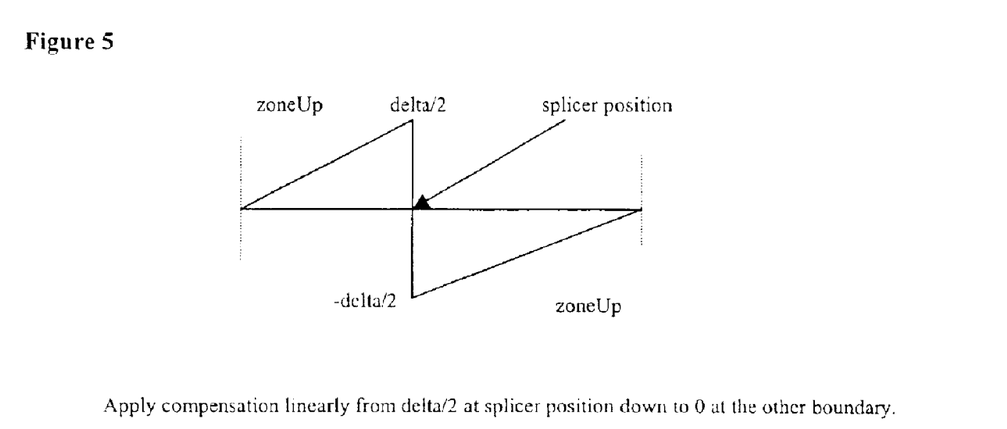
FIG. 5 shows applying intensity compensation in accordance with an embodiment of the present invention.

In an embodiment, compensation may be applied to an entire zone. However, banding may occur near the splicer position, and the compensation may not apply to an entire focal zone equally. Instead, in an embodiment, compensation may be applied in a linearly-decreasing fashion, as shown in FIG. 5. In an alternative embodiment, first and last focal zones in an image may be compensated differently. For example, to prevent creation of excessive noise, the difference may be applied to half of the zone in a linearly-decreasing fashion.

If the method 400 is being used ("turned on") and if the compensation fluctuates from frame to frame (caused by image noise or certain patient anatomy, for example), the image may be flickering. At step 450, a filter, such as a temporal Infinite Impulse Response (IIR) filter, may be applied (similar to frame averaging) to the current and previous frames to avoid flickering in the image. An example of a filter is illustrated in equation (1):

$$Y_{out} = 0.5 * X_{current} + 0.5 * Y_{previous} \quad (1).$$

In certain embodiments, coefficients may have values other than (0.5, 0.5), such as (0.4, 0.6), etc.

In certain embodiments, when a certain condition occurs, the filter is initialized. For example, if image depth changes, focal zone position changes, number of focal zones changes, imaging frequency changes (from 4 MHz to 6 MHZ, for example), and/or application changes (from thyroid to breast imaging, for example), then the filter may be initialized. Compensation values may be initialized for each zone using values computed from the first focal region after a change occurs. However, if all values are initialized down to zero, initialization may cause some intermittent banding.

At step 460, image data may be clipped if the image data exceeds or falls below a certain threshold. Then, at step 470, the next splicer position at which focal zones are combined may be examined and the method 400 may be repeated.

Certain embodiments of the present invention suppress banding by processing the incoming detected and log-compressed data from the B-mode processor 30 in real-time to extract and compensate the median/mean image intensity difference between adjacent zones. Preferably, the method described in certain embodiments of the present invention is activated for images with at least two focal zones. Certain embodiments reduce banding in real-time using faster processing of signal and image data compared with current methods. Certain embodiments result in more accurate and efficient banding reduction for banding caused by waveforms/frequency/f-number and/or patient habitus (a patient's body build and health, particularly a patient's predisposition to disease), for example. Rather than applying a constant gain compensation across an entire zone, certain embodiments split the gain difference in half and apply ramp-compensation on the split gain difference. Additionally, in certain embodiments, data thresholds may be based on different applications, contrary to the prior art. In certain embodiments, banding suppression may be accomplished using a software-based implementation, for example, rather than by the addition of extra, more complicated, and slower hardware. Certain embodiments of the present invention may be applied to all B-mode applications.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A system for reducing banding artifacts in an ultrasound image, said system comprising:

a transducer for transmitting ultrasound energy to a subject and receiving echoes from the subject;

a front-end for producing data from the received echoes; and a processor for processing the data to produce an image, the processor combining data from at least a first focal zone and a second focal zone, wherein the processor excludes extreme data points and determines a difference in intensity between data in the first focal zone and data in the second focal zone, the processor applying the difference to at least one of the first focal zone and the second focal zone.

2. The system of claim 1, wherein the front-end comprises a receiver, a transmitter, and a beamformer.

3. The system of claim 1, wherein the processor comprises a B-mode processor for B-mode imaging.

4. The system of claim 1, wherein the processor comprises a control processor for executing functions for operational modes.

5. The system of claim 1, wherein the processor comprises a display processor for processing digital data for display.

6. The system of claim 1, wherein the processor accommodates a plurality of imaging and diagnostic modes.

7. The system of claim 1, further comprising a display for formatting and displaying data.

8. A method for reducing banding artifacts in an ultrasound image, said method comprising:

examining a border between a first focal zone and a second focal zone in a combined ultrasound image;

selecting a first subset of data adjacent to the border in the first focal zone and a second subset of data adjacent to the border in the second focal zone;

excluding extreme data points within the first and second subsets of data;

determining a first intensity level for the first subset of data and a second intensity level for the second subset of data;

determining a difference between the first intensity level and the second intensity level; and applying the difference to at least one of the first focal zone and the second focal zone.

9. The method of claim 8, wherein the first intensity level comprises a mean or median intensity value for the first focal zone.

10. The method of claim 8, wherein the second intensity level comprises a mean or median intensity value for the second focal zone.

11. The method of claim 8, wherein the difference is split equally and applied to the first focal zone and the second focal zone.

12. The method of claim 8, wherein the difference is not applied if a dark pixel threshold is exceeded.

13. The method of claim 8, wherein the difference is not applied if the difference is less than a minimum threshold or greater than a maximum threshold.

14. The method of claim 8, further comprising applying a filter to the difference and an intensity difference for a previous frame.

15. The method of claim 8, further comprising displaying the combined ultrasound image.

16. A method for banding suppression in a B-mode ultrasound image, said method comprising:

processing a first focal region to determine intensity of first focal region image data;

determining a difference in intensity between first focal region image data and second focal region image data surrounding a border between the first focal region and a second focal region;

applying a filter to current and previous frames to minimize flickering in the image; and adjusting intensity of image data in the second focal region based on the difference in intensity.

17. The method of claim 16, wherein the determining step comprises determining a difference in median or mean intensity between first focal region image data and second focal region image data surrounding a border between the first focal region and a second focal region.

18. The method of claim 16, wherein the difference is split equally and applied to the first focal region and the second focal region.

19. The method of claim 16, wherein intensity of image data is not adjusted if at least one of a dark pixel threshold is exceeded, the difference is less than a minimum threshold, and the difference is greater than a maximum threshold.

20. The method of claim 16, further comprising applying a filter to the difference in intensity and a difference in intensity for a previous frame.

21. A method for reducing banding artifacts in an ultrasound image, said method comprising:

examining a border between a first focal zone and a second focal zone in a combined ultrasound image;

selecting a first subset of data adjacent to the border in the first focal zone and a second subset of data adjacent to the border in the second focal zone;

determining a first intensity level for the first subset of data and a second intensity level for the second subset of data;

determining a difference between the first intensity level and the second intensity level; and applying the difference to at least one of the first focal zone and the second focal zone, wherein the difference is not applied if a dark pixel threshold is exceeded.

22. A method for reducing banding artifacts in an ultrasound image, said method comprising:

examining a border between a first focal zone and a second focal zone in a combined ultrasound image;

selecting a first subset of data adjacent to the border in the first focal zone and a second subset of data adjacent to the border in the second focal zone;

determining a first intensity level for the first subset of data and a second intensity level for the second subset of data;

determining a difference between the first intensity level and the second intensity level; and applying the difference to at least one of the first focal zone and the second focal zone, wherein the difference is not applied if the difference is less than a minimum threshold or greater than a maximum threshold.

23. A method for reducing banding artifacts in an ultrasound image, said method comprising:

examining a border between a first focal zone and a second focal zone in a combined ultrasound image;

selecting a first subset of data adjacent to the border in the first focal zone and a second subset of data adjacent to the border in the second focal zone;

determining a first intensity level for the first subset of data and a second intensity level for the second subset of data;

determining a difference between the first intensity level and the second intensity level;

applying the difference to at least one of the first focal zone and the second focal zone; and applying a filter to the difference and an intensity difference for a previous frame.

24. A method for banding suppression in a B-mode ultrasound image, said method comprising:

processing a first focal region to determine intensity of first focal region image data;

determining a difference in intensity between first focal region image data and second focal region image data surrounding a border between the first focal region and a second focal region; and adjusting intensity of image data in the second focal region based on the difference in intensity, wherein the difference is split equally and applied to the first focal region and the second focal region.

25. A method for banding suppression in a B-mode ultrasound image, said method comprising:

processing a first focal region to determine intensity of first focal region image data;

determining a difference in intensity between first focal region image data and second focal region image data surrounding a border between the first focal region and a second focal region; and adjusting intensity of image data in the second focal region based on the difference in intensity, wherein intensity of image data is not adjusted if at least one of a dark pixel threshold is exceeded, the difference is less than a minimum threshold, and the difference is greater than a maximum threshold.

* * * * *

UNITED STATES PATENT AND TRADEMARK OFFICE
CERTIFICATE OF CORRECTION

PATENT NO. : 6,893,399 B2
DATED : May 17, 2005
INVENTOR(S) : Panda et al.

It is certified that error appears in the above-identified patent and that said Letters Patent is hereby corrected as shown below:

Column 1,
Line 26, delete "2.5-MHz" and substitute therefore -- 2.5-10MHz --.

Signed and Sealed this

Sixth Day of September, 2005

JON W. DUDAS
*Director of the United States Patent and Trademark Office*